(12) United States Patent
Kwon et al.

(10) Patent No.: US 10,653,624 B2
(45) Date of Patent: May 19, 2020

(54) DELIVERY METHOD OF TARGET MATERIAL INTO EXTRACELLULAR VESICLES USING EXTRACORPOREAL SHOCKWAVE

(71) Applicant: Exollence Biotechnology Co., Ltd., Yangchun-gu, Seoul (KR)

(72) Inventors: Kihwan Kwon, Seoul (KR); Jihwa Chung, Gyeonggi-do (KR); Kyounghwa Kim, Seoul (KR)

(73) Assignee: EXOLLENCE BIOTECHNOLOGY CO., LTD., Seoul (KR)

( * ) Notice: Subject to any disclaimer, the term of this patent is extended or adjusted under 35 U.S.C. 154(b) by 0 days.

(21) Appl. No.: 15/995,638

(22) Filed: Jun. 1, 2018

(65) Prior Publication Data
US 2018/0344643 A1 Dec. 6, 2018

(30) Foreign Application Priority Data

Jun. 2, 2017 (KR) .................. 10-2017-0069309
May 16, 2018 (KR) .................. 10-2018-0055994

(51) Int. Cl.
| | |
|---|---|
| C07H 21/04 | (2006.01) |
| A61K 9/127 | (2006.01) |
| C12N 13/00 | (2006.01) |
| A61K 41/00 | (2020.01) |
| A61K 47/69 | (2017.01) |
| C12N 15/88 | (2006.01) |
| C12N 15/113 | (2010.01) |
| C12N 15/87 | (2006.01) |
| C12N 15/11 | (2006.01) |

(52) U.S. Cl.
CPC ........ *A61K 9/1271* (2013.01); *A61K 41/0028* (2013.01); *A61K 47/6907* (2017.08); *C12N 13/00* (2013.01); *C12N 15/113* (2013.01); *C12N 15/87* (2013.01); *C12N 15/88* (2013.01); *C12N 15/111* (2013.01); *C12N 2310/14* (2013.01); *C12N 2310/141* (2013.01); *C12N 2310/3517* (2013.01); *C12N 2320/32* (2013.01)

(58) Field of Classification Search
None
See application file for complete search history.

(56) References Cited

FOREIGN PATENT DOCUMENTS

| KR | 1020110029195 | 3/2011 |
|---|---|---|
| KR | 1020160006974 | 1/2016 |

OTHER PUBLICATIONS

Holfeld, Johannes, et al. "Shockwave therapy differentially stimulates endothelial cells: implications on the control of inflammation via toll-like receptor 3." Inflammation 37.1 (2014): 65-70.*
Ha, et al (Scientific Reports, 5, 12843, 2015).*
Mariotto, et al (Nitric Oxide, 12, 89-96, 2005).*

* cited by examiner

*Primary Examiner* — Kimberly Chong
(74) *Attorney, Agent, or Firm* — Sughrue Mion, PLLC

(57) ABSTRACT

The present disclosure relates to a method of delivering target materials into extracellular vesicles including exposing the target materials and the extracellular vesicles to extracorporeal shockwaves, a method of preparing target material-introduced extracellular vesicles, extracellular vesicles prepared by the method, drug delivery vehicles including extracellular vesicles, and a method of delivering target materials into cells. The present disclosure exposes extracellular vesicles derived from natural organisms such as animal cells, plant cells, and microorganisms including bacteria and eukaryotic bacteria as well as artificially produced extracellular vesicles to extracorporeal shockwaves extracellularly. Thus, the high-level energy extracorporeal shockwaves can be used to deliver the target material into the extracellular vesicle efficiently. When treating with extracorporeal shockwaves, the ability of target material-introduced extracellular vesicles to incorporate into target cells also increases. According to the method of the present disclosure, the target materials can be delivered into cells with high efficiency, being utilized in various fields.

5 Claims, 11 Drawing Sheets

Specification includes a Sequence Listing.

SEQUENCE LISTING

<160> NUMBER OF SEQ ID NOS: 2

<210> SEQ ID NO 1
<211> LENGTH: 17
<212> TYPE: DNA

```
<213> ORGANISM: Artificial Sequence
<220> FEATURE:
<223> OTHER INFORMATION: U6-Fw PCR primer

<400> SEQUENCE: 1
ctcgcttcgg cagcaca                                                 17

<210> SEQ ID NO 2
<211> LENGTH: 22
<212> TYPE: DNA
<213> ORGANISM: Artificial Sequence
<220> FEATURE:
<223> OTHER INFORMATION: Mature Cel-miR-39 PCR Primer

<400> SEQUENCE: 2
agctgatttc gtcttggtaa ta                                           22
```

DELIVERY METHOD OF TARGET MATERIAL INTO EXTRACELLULAR VESICLES USING EXTRACORPOREAL SHOCKWAVE

REFERENCE TO RELATED APPLICATIONS

This application is based on and claims priority from Korean Patent Application No. 10-2017-0069309, filed on Jun. 2, 2017, and Application No. 10-2018-0055994, filed on May 16, 2018 with the Korean Intellectual Property Office, the disclosure of which is incorporated herein in its entirety by reference.

TECHNICAL FIELD

The present disclosure relates to a method of delivering a target material into an extracellular vesicle, which includes exposing the target material and the extracellular vesicle to an extracorporeal shockwave, a method of preparing a target material-introduced extracellular vesicle, an extracellular vesicle prepared by the method, a drug delivery vehicle including an extracellular vesicle, and a method of delivering a target material into a cell.

BACKGROUND

Shockwaves are continuous single soundwaves generated by a specific soundwave generator, which have a high peak pressure amplitude of up to 100 MPa and a short duration of less than 1 μm. Further, shockwaves can deliver to a specific target area with an energy density in the range of 0.005 mJ/mm² to 1.0 mJ/mm².

High-energy extracorporeal shock-wave lithotripsy (ESWL) is a kind of treatment for breaking stones in the kidney and bile duct by applying pressure of 35 MPa to 100 MPa to the target area of the human body. New treatments have been attempted in a variety of fields since such method was first tried. Recently, it has been reported that extracorporeal shock-wave lithotripsy is used in the treatment of musculoskeletal diseases and is useful for anti-inflammatory action and blood flow increase.

Extracellular vesicles are nanoparticles vesicles composed of a bilayer lipid membrane, which have several tens of nanometers to several hundreds of nanometers. Further, they are composed of biologically active substances such as proteins, lipids, and genes. In the past, they were regarded as debris secreted from the cells, but they are now considered clinically meaningful. Therefore, various studies about the extracellular vesicles are actively going on. In particular, exosomes, which are the spherical follicles released by cells, have lots of information about the mother cell protein and DNA, etc. Thus, it has been actively attempted to develop a marker and a sensor to detect cancer using the same as a biomarker. For example, studies have suggested the diagnosis of glioblastoma based on the detection of EGFRVIII genes, a form mutated from extracellular vesicles present in the patient's blood. There are also studies that have confirmed the presence of prostate cancer biomarkers PCA-3 and TMPRSS2:ERG in extracellular vesicles present in the patient's urine through the genomic analysis of extracellular vesicles derived from cancer cells. Further, Korean Patent No.: 10-1704828 discloses a method for diagnosing an inflammatory disease by analyzing the expression level of inflammatory-related disease genes which present in extracellular vesicles in body fluids.

Meanwhile, the present inventors have found, before suggesting the present disclosure, that the production and secretion of extracellular vesicles such as exosomes, ectosomes, microvesicles or apoptotic bodies into which desired target materials are introduced by treating with extracorporeal shockwaves, thereby establishing a method of preparing cells including the target materials in Korean Patent No.: 10-1719569. However, this method confirms that extracellular vesicles produced by extracorporeal shockwave applied to cells are only medium in the transformation process but does not disclose a mechanism of using extracellular vesicles, especially exosomes themselves and a transformation method using the same directly. Compared with cell-based therapies, exosome-based drug deliveries or therapies may have no vascular obstructive effect and may reduce the risk of secondary microvascular thrombosis and the risk of tumor formation. Further, exosomes can be obtained in a large number through a small number of cells. A large number of exosomes obtained as described above have many merits that they are stable, easy to store, do not induce an immune rejection reaction, thereby easily applying in clinical practice. Therefore, there is a need to study cell treatment using exosomes themselves, which is improved compared to cell-mediated therapies.

SUMMARY

The present inventors had studied a method of delivering a target material into an extracellular vesicle which is a medium for delivering the target material during a transformation process. They have found that unlike convention techniques disclosed in Korean Patent No. 10-1719569, an extracellular vesicle was treated with an extracorporeal shockwave with a high energy level to increase the introduction rate of the target material into the extracellular vesicle and the incorporation of the target material-introduced extracellular vesicle into a cell. Further, they have confirmed that extracellular vesicles derived from natural organisms such as animal cells, plant cells, and microorganisms including bacteria and eukaryotic bacteria as well as artificially produced extracellular vesicles may be used as extracellular vesicles including target materials. Further, they have found that the extracorporeal shockwave was used, leading to an increase in efficiency of delivering the target material to the desired cell. Thus, the present disclosure has been completed.

The present disclosure has been made in an effort to provide a method of delivering a target material into an extracellular vesicle including exposing the target material and the extracellular vesicle to an extracorporeal shockwave, a method of preparing a target material-introduced extracellular vesicle, an extracellular vesicle prepared by the method, a drug delivery vehicle including an extracellular vesicle, and a method of delivering a target material into a cell.

An exemplary embodiment of the present disclosure provides a method of delivering a target material into an extracellular vesicle, which includes exposing the target material and the extracellular vesicle to an extracorporeal shockwave.

Another exemplary embodiment of the present disclosure provides a method of preparing a target material-introduced extracellular vesicle, which includes exposing the target material and the extracellular vesicle to an extracorporeal shockwave.

Yet another exemplary embodiment of the present disclosure provides an extracellular vesicle prepared by the method as described above.

Yet another exemplary embodiment of the present disclosure provides a drug delivery vehicle including the extracellular vesicle as described above.

Yet another exemplary embodiment of the present disclosure provides a method of delivering a target material into a cell, which includes (a) exposing the target material and an extracellular vesicle to an extracorporeal shockwave to introduce the target material into the extracellular vesicle and (b) treating the cell with the target material-introduced extracellular vesicle.

According to the exemplary embodiments of the present disclosure, extracellular vesicles derived from natural organisms such as such as animal cells, plant cells, and microorganisms including bacteria and eukaryotic bacteria as well as artificially produced extracellular vesicles are exposed to an extracorporeal shockwave extracellularly. Thus, the high-level energy extracorporeal shockwave can be used to deliver the target material into the extracellular vesicle efficiently. Further, when applying the extracorporeal shockwave, the ability of the target material-introduced extracellular vesicle to incorporate into the target cell also increases. As a result, the target material can be delivered into the cell with high efficiency, which can be utilized in various fields.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
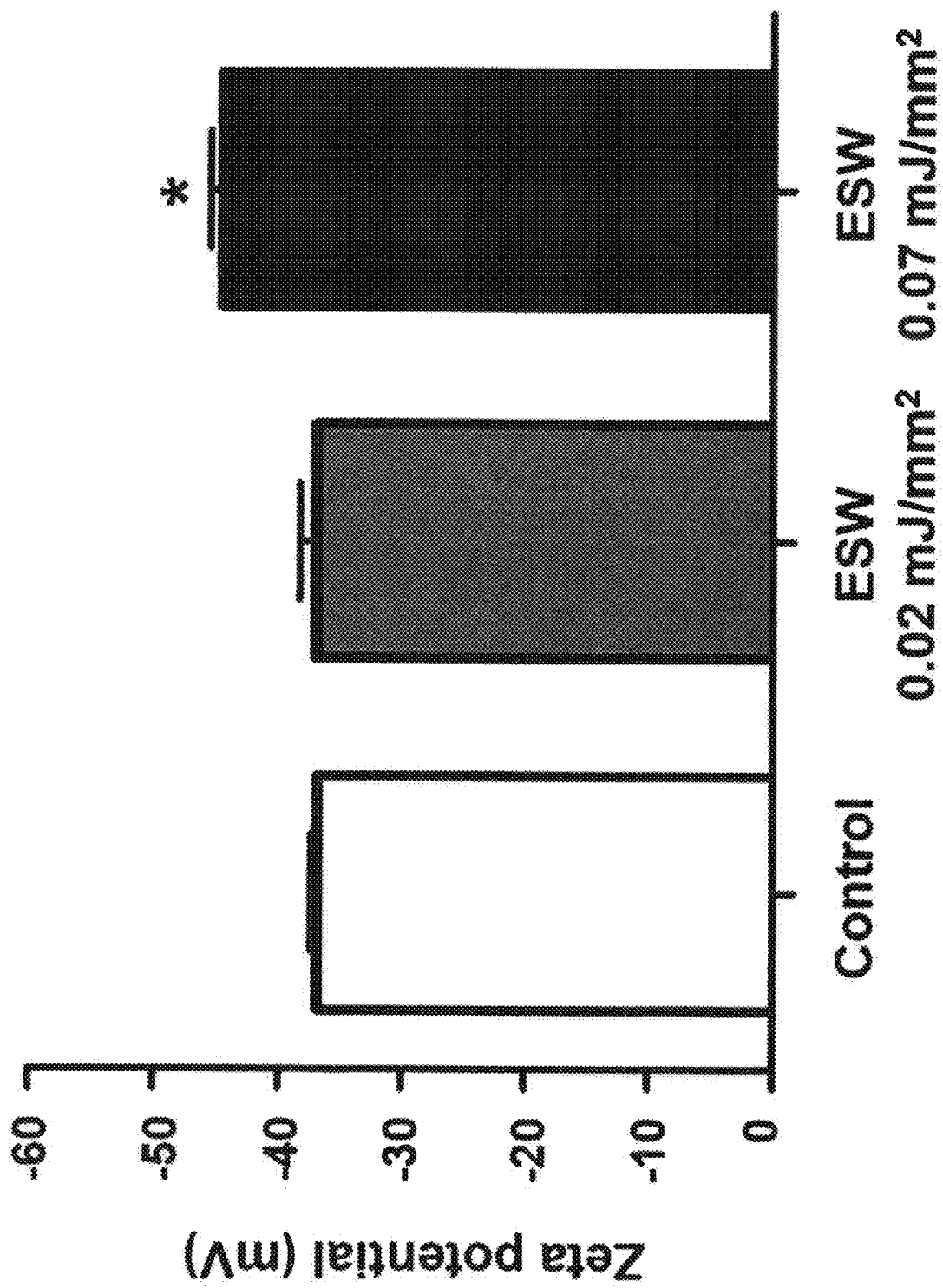
FIG. 1 is a view illustrating the results of measuring the change in zeta potential of an exosome dispersion solution with or without extracorporeal shockwave treatment.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

The present disclosure may provide a method of delivering a target material into an extracellular vesicle, which includes exposing the target material and the extracellular vesicle to an extracorporeal shockwave.

Hereinafter, the present disclosure is described in more detail.

The term "target material" used in the present disclosure may, without limitation, include a substance which is transferred into cells to exhibit their desired effects. Preferably, the target material may include at least one selected from the group consisting of nucleic acids, proteins, and compound. Further, the nucleic acids may include naturally occurring nucleic acids or artificially produced nucleic acids. Preferably, the nucleic acids may, but be not limited to, include DNA, RNA, microRNA (miRNA), small RNA (smRNA), small interfering RNA (siRNA), piwi-interacting RNA (piRNA), small nucleolar RNA (snoRNA), tRNA-derived small RNA (tsRNA), small rDNA-derived RNA (srRNA), small nuclear RNA (U-RNA), and long noncoding RNA (lncRNA).

The term "extracorporeal shockwave" used in the present disclosure refers to a continuous single sound wave generated by a specific sound generator, which has a high peak pressure amplitude of up to 100 MPa, has a short duration of less than 1 μs, and delivers to a specific target area with an energy density in the range of 0.005 mJ/mm$^2$ to 1.0 mJ/mm$^2$. Unlike the conventional techniques disclosed in Korean Patent No. 10-1719569, exosomes are treated with extracorporeal shockwaves in the present disclosure. In the conventional patent, living cells died when treated with the extracorporeal shockwave having 0.09 mJ/mm$^2$ or more. However, the extracorporeal shockwave having 0.09 mJ/mm$^2$ or more can be utilized in the present disclosure. Further, the present disclosure has a merit that the extracorporeal shockwave having 0.05 mJ/mm$^2$ or more can be used although its effect has not been confirmed in detail in embodiments of the conventional patent.

An embodiment of the present disclosure confirms that the high energy level extracorporeal shockwave having 0.05 mJ/mm$^2$ or more is used, resulting in an increase in introduction rate of target materials into the extracellular vesicles and the ability of incorporation of the target material-introduced extracellular vesicles into cells. It also confirms an increase in the efficiency of delivering target materials into desired cells. Further, it confirms that extracellular vesicles obtained from plant cells may be used as well as animal cell-derived extracellular vesicles, thereby expanding their use for drug delivery vehicles.

Thus, the extracorporeal shockwave used in the present disclosure may be treated in an energy range of 0.05 mJ/mm$^2$ to 0.9 mJ/mm$^2$, specifically 0.05 mJ/mm$^2$ to 0.89 mJ/mm$^2$, more specifically 0.05 mJ/mm$^2$ to 0.70 mJ/mm$^2$. The strength of the extracorporeal shockwave may vary depending on the volume of the extracellular vesicle to which the extracorporeal shockwave is applied, the type of cells from which the extracellular vesicle is made, and the type of extracellular vesicle produced. In one embodiment of the present disclosure, an extracellular vesicle is treated with the extracorporeal shockwave having an intensity of 0.07 mJ/mm$^2$ or more.

The term "extracellular vesicle" used in the present disclosure refers to small globules surrounded by membranes derived from cells, and these globules vary greatly depending on the origin of the cells or how they are made. In the present disclosure, the extracellular vesicle may, but be not limited to, include any one selected from the group consisting of exosomes, ectosomes, microvesicles and apoptotic bodies, which are named according to the method the cells are made. The extracellular vesicle may be an extracellular vesicle derived from natural world such as plants, animals, and microorganisms or an extracellular vesicle artificially produced. Further, the extracellular vesicle may be a cell isolated from a natural organism. Further, the cell may be derived from any type of plants or animals including human and non-human mammals. Further, the cell may be various types of immune cells, tumor cells, and the like. Further, in one embodiment of the present disclosure, the cell may include a human umbilical vein endothelial cell (HUVEC), a mesenchymal stem cell (MSC) or a vascular smooth muscle cell (VSMC).

Further, the present inventors have selected an exosome as an extracellular vesicle in one embodiment of the present disclosure. The exosome may be derived from plants or animals. A target material may be introduced into the exosome, thereby delivering the target material into the extracellular vesicle efficiently.

Therefore, it is confirmed that the introduction of the target material into the extracellular vesicle by applying the extracorporeal shockwave may be more efficient than cases without applying the extracorporeal shockwave. Further, it is confirmed that the target material-introduced extracellular vesicle may exhibit excellent transformation efficiency into other cells. Therefore, the method of the present disclosure can be applied to various fields related thereto.

Further, the present disclosure may provide a method of preparing the target material-introduced extracellular vesicle, which includes exposing the target material and the extracellular vesicle to the extracorporeal shockwave.

In the method of preparing the target material-introduced extracellular vesicle of the present disclosure, the extracorporeal shockwave may be treated in an energy range of 0.05 mJ/mm$^2$ to 0.9 mJ/mm$^2$, specifically 0.05 mJ/mm$^2$ to 0.89 mJ/mm$^2$, more specifically 0.05 mJ/mm$^2$ to 0.70 mJ/mm$^2$ so that the target material can be efficiently introduced into cells. In one embodiment of the present disclosure, the extracorporeal shockwave may be treated to the extracellular vesicle with an intensity of 0.07 mJ/mm$^2$ or more to prepare the target material-introduced extracellular vesicle efficiently.

In the method of the present disclosure, the extracellular vesicle may, but be not limited to, include any one selected from the group consisting of exosomes, ectosomes, microvesicles, and apoptotic bodies. The extracellular vesicle may be derived from a natural organism including any plant, animal and microorganism having an extracellular vesicle or artificially produced. An exosome is used in one embodiment of the present disclosure.

Further, the present disclosure may provide an extracellular vesicle prepared by the method as described above.

The target material may be transferred to the extracellular vesicle without destroying the extracellular vesicle when using the extracellular vesicle prepared by the method of preparing the target material-introduced extracellular vesicle, which includes exposing the target material and the extracellular vesicle to the extracorporeal shockwave according to the present disclosure.

In one embodiment of the present disclosure, a case of treating with extracorporeal shockwave at 0.02 mJ/mm$^2$ may not differ from control groups untreated with extracorporeal shockwave. However, a case of treating with extracorporeal shockwave energy level of 0.07 mJ/mm$^2$ may exhibit increased zeta potential of an exosome dispersion solution by 20% or more compared with control groups. Further, it is confirmed that the exosome size distribution in one embodiment of the present disclosure may be different from that of the extracellular vesicles prepared by the method. This demonstrates that the exosome size distribution is changed due to the extracorporeal shockwave. The result confirms that the physical properties of the extracellular vesicle itself can be changed within the range that does not affect the incorporation of the extracellular vesicle into the desired cell.

Further, the extracellular vesicle prepared by the method of the present disclosure is characterized by the increased ability of incorporation into cells and increased zeta potential compared with the control group which is not exposed to the extracorporeal shockwave.

Further, the present disclosure may provide a drug delivery vehicle including the extracellular vesicle.

Using the extracellular vesicle prepared by the method of the present disclosure method, the target material may be delivered to the extracellular vesicle without destroying the extracellular vesicle. This may result in efficient delivery of the target material into the desired cell, thereby preparing drug delivery vehicles efficiently.

Therefore, the extracellular vesicle according to the present disclosure may be characterized by an increased ability of incorporation into the cell. Thus, the drug delivery vehicle of the present disclosure may be used to perform the intracellular delivery effectively and to deliver the target material into the desired cell efficiently, thereby achieving the purpose such as the treatment of diseases.

A drug that can be carried on the drug delivery vehicle of the present disclosure may, without limitation, include a target material that can be delivered into the exosome by the extracorporeal shockwave, that is, a substance capable of expressing its intended effects by being delivered into cells. Preferably, the target material may include at least one selected from the group consisting of nucleic acids, proteins, and compound. Further, the nucleic acids may include naturally occurring nucleic acids or artificially produced nucleic acids. Preferably, the nucleic acids may, but be not limited to, include DNA, RNA, microRNA (miRNA), small RNA (smRNA), small interfering RNA (siRNA), piwi-interacting RNA (piRNA), small nucleolar RNA (snoRNA), tRNA-derived small RNA (tsRNA), small rDNA-derived RNA (srRNA), small nuclear RNA (U-RNA), and long noncoding RNA (lncRNA).

Further, the present disclosure may provide a method of delivering a target material into a cell, which includes (a) exposing the target material and an extracellular vesicle to an extracorporeal shockwave to introduce the target material into the extracellular vesicle and (b) treating the cell with the target material-introduced extracellular vesicle.

Using a method of delivering the target material into the cell of the present disclosure may increase the ability of the target material-introduced extracellular vesicle to incorporate into the cell, thereby increasing delivery of the target material into the desired cell. Further, extracellular vesicles obtained from plant cells as well as animal cells can be used without limitation, thereby expanding the utility as a drug delivery vehicle.

In step (a) of the method of delivering the target material into the cell of the present disclosure, the extracorporeal shockwave may be treated in an energy range of 0.05 mJ/mm$^2$ to 0.9 mJ/mm$^2$, specifically 0.05 mJ/mm$^2$ to 0.89 mJ/mm$^2$, more specifically 0.05 mJ/mm$^2$ to 0.70 mJ/mm$^2$.

Hereinafter, in order to readily understand the present disclosure, Examples are described in detail. However, the following Examples are merely illustrative of the contents of the present disclosure, and the scope of the present disclosure is not limited thereto. Examples of the present disclosure are provided to allow those skilled in the art to more thoroughly understand the present disclosure.

Example 1. Isolation of Exosome

Isolation of Exosome Derived from Various Cells (HUVEC, MSC, and VSMC)

In order to isolate exosomes derived from human umbilical vein endothelial cells (HUVECs), HUVECs were incubated in M200 medium including 5% FBS and 1% antibiotic/antifungal agent at 5% $CO_2$ and 37° C. In this Example, the cells were sub-cultured on a plate having a diameter of 10 cm every 2 days to 3 days. In order to isolate exosomes from the cells, the debris of the medium was removed, and then exosomes were isolated using a syringe filter having a size of 0.2 μM pore. The exosome isolation experiments were performed using exosome-removed FBS centrifuged at 32,000 rpm for 1 hour and 30 minutes. The isolated exosomes were centrifuged at 3,000 g for 30 minutes, concentrated, and used after confirming by nanoparticle tracking analysis (NTA).

In order to isolate exosomes from the mesenchymal stem cells (MSCs) or the vascular smooth muscle cells (VSMCs), only MSC or VSMC was used as the isolating starting cell. Except that, exosomes were isolated in the same manner as the method of isolating exosomes from HUVECs.

Isolation of Exosome from Milk and Grapefruit

Milk and grapefruit were selected as animal-derived and plant-derived sources that can obtain many exosomes other than cells, and exosomes were isolated from them. In order to isolate exosomes derived from milk, commercially available milk was purchased and used. After centrifugation at 20,000 g for 2 hours, the cream layer was removed. Then, exosomes were isolated by density gradient centrifugation (OptiPrep). For isolation, 0.5 ml of 50% OptiPrep was put at the bottom of the centrifuge tube, 1 ml of 10% OptiPrep was put at the top thereof, and 10 ml of milk was put at the top thereof. Therefore, centrifugation was performed at 100,000 g for 16 hours to isolate exosomes obtained between 50%-layer and 10%-layer.

In order to isolate exosomes derived from grapefruit, grapefruit juice was used. After two centrifugations at 3,000 g for 30 minutes, the debris was removed. Then, exosomes were isolated by OptiPrep. For isolation, 1 ml of 50% OptiPrep was put at the bottom of the centrifuge tube, 1 ml of 10% OptiPrep was put at the top thereof, and 10 ml of grapefruit juice was put at the top thereof. Therefore, centrifugation was performed at 100,000 g for 2 hours to isolate exosomes obtained between 50%-layer and 10%-layer.

The exosomes were isolated from the milk and grapefruit and were confirmed by nanoparticle tracking analysis (NTA). Then the exosomes were used.

Exosomes isolated from cells, animal-derived materials, and plant-derived materials were used in the following Examples.

Example 2. Change of Exosome's Physical Properties by Extracorporeal Shockwave Treatment 2.1 Confirmation of Change of Exosome Zeta Potential by Extracorporeal Shockwave Treatment Experiments were conducted to measure the change of zeta potential, which is particle's surface potential, depending on energy levels of extracorporeal shockwave in order to confirm the change of exosome's physical properties when applying extracorporeal shockwave.

The isolated exosomes which were derived from HUVEC were included in 1×1010 cells per well for each experimental group. The experimental group was untreated with the extracorporeal shockwave or was treated with the extracorporeal shockwave having an energy level of 0.02 mJ/mm$^2$ and 0.07 mJ/mm$^2$. Change of zeta potential of the exosome dispersion solution with or without extracorporeal shockwave treatment was measured using ELSZ-2000 device (Otsuka Electronics Co., Ltd.), which is a device for measuring zeta potential. The results are illustrated in FIG. 1.

As illustrated in FIG. 1, when applying the extracorporeal shockwave at 0.02 mJ/mm$^2$, there was no difference compared with the extracorporeal shockwave untreated control groups. However, when applying the extracorporeal shockwave at 0.07 mJ/mm$^2$, the zeta potential value was increased by 20% or more compared with control groups. The increase in the absolute value of the zeta potential demonstrates that the colloidal particles suspended in the liquid become larger in electrical repulsion to result in floating uniformly in the liquid without agglomeration phenomenon. When exosomes were treated with the extracorporeal shockwave of 0.05 ml/mm$^2$ or more, it was confirmed that the electrical repulsion of the colloidal particles of the exosome dispersion solution was stronger, indicating that the extracorporeal shockwave treatment induces the change of physical properties of exosomes.

2.2 Confirmation of Change of Exosome Size by Extracorporeal Shockwave Treatment To confirm whether the physical properties of exosomes changed when extracorporeal shockwave treatment was applied, the effect of exosome's size, one of their physical properties, was confirmed. Exosomes isolated from HUVEC were put into wells to be 3×10$^9$ cells per well. In control groups, there were no extracorporeal shockwave treatments. In addition, extracorporeal shockwave treatments were performed with various energy levels at 0.02 mJ/mm$^2$, 0.07 mJ/mm$^2$, 0.09 mJ/mm$^2$ and 0.12 mJ/mm$^2$, respectively.

Then, a nanoparticle tracking analysis (NTA) device was used to measure the change of exosome size by presence or absence of extracorporeal shockwave treatment. The change of exosome size is illustrated in FIG. 2.

Figure 2:
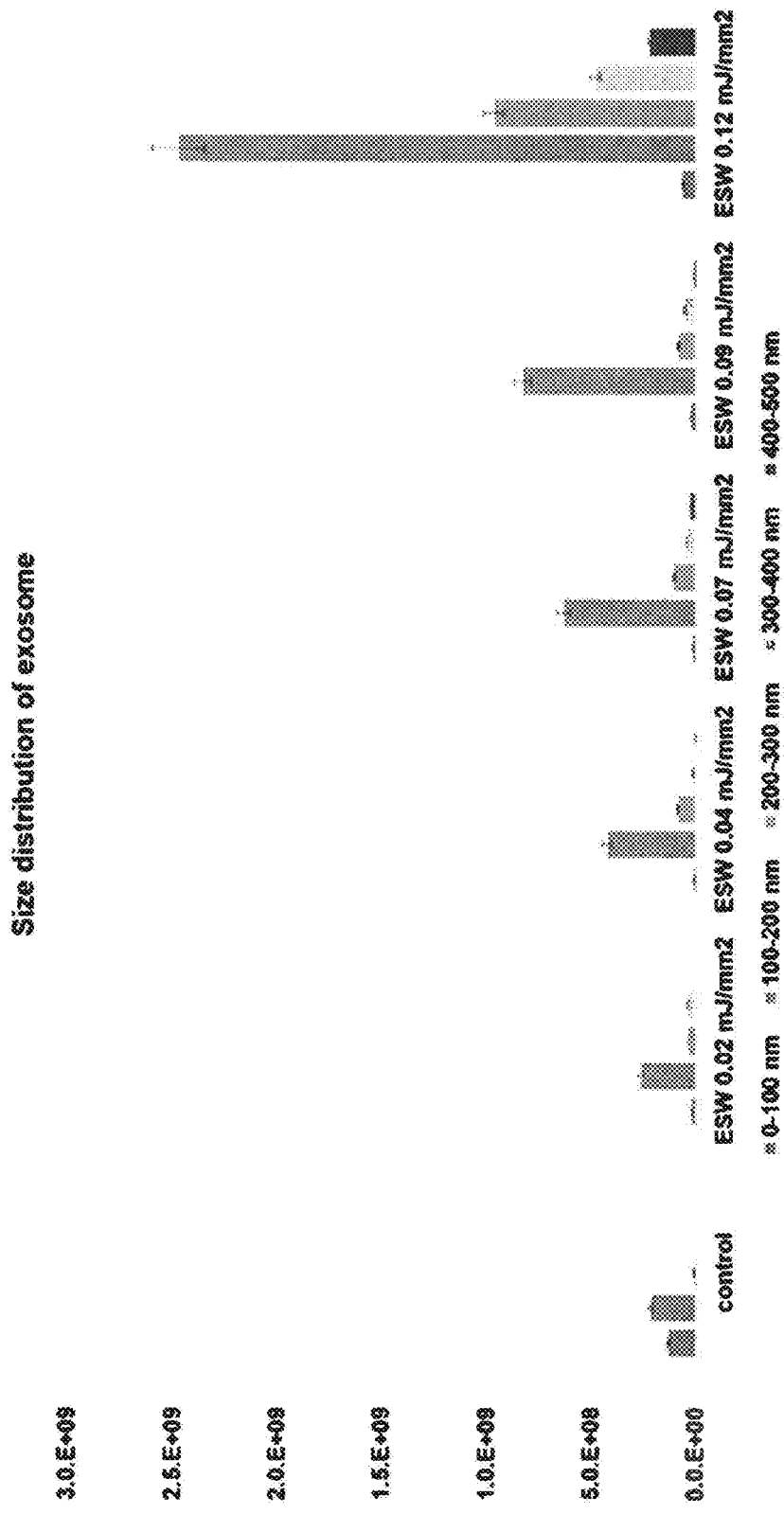
FIG. 2 is a view illustrating the results of measuring the change in exosome size with or without extracorporeal shockwave treatment using a nanoparticle tracking analysis (NTA) device.

As illustrated in FIG. 2, as the energy level of the extracorporeal shockwave increases, the number of exosomes having 100 nm to 200 nm after the extracorporeal shockwave treatment tends to increase significantly. Especially, when the energy level of 0.12 $mJ/mm^2$ was applied, the number of exosomes having 100 nm to 200 nm was increased about 10 times as compared with that of the control groups, and the number of exosomes having 200 nm or more was also remarkably increased. These demonstrate that the exosome size distribution changes differently when exosomes are treated with extracorporeal shockwaves, resulting in confirming the change of exosome's physical property in which their types of the exosome size distribution are different due to the extracorporeal shockwaves.

2.3 Confirmation of Increase of Incorporation Ability of HUVEC-Derived Exosome by Extracorporeal Shockwave Exosomes derived from HUVEC, human vascular endothelial cells, isolated in Example 1 were put into wells to be $3 \times 10^9$ cells per well. The exosomes were stained with PKH26. In control groups, there were no extracorporeal shockwave treatments. In addition, extracorporeal shockwave treatments were performed with various energy levels at 0.02 $mJ/mm^2$, 0.07 $mJ/mm^2$, 0.09 $mJ/mm^2$ and 0.12 $mJ/mm^2$, respectively. HUVECs, human vascular endothelial cells, were treated with the extracorporeal shockwave-treated exosome. After one hour, the exosome's incorporation into the desired cells according to the extracorporeal shockwave energy level was compared and analyzed. The results of the experiment are illustrated in FIG. 3.

Figure 3:
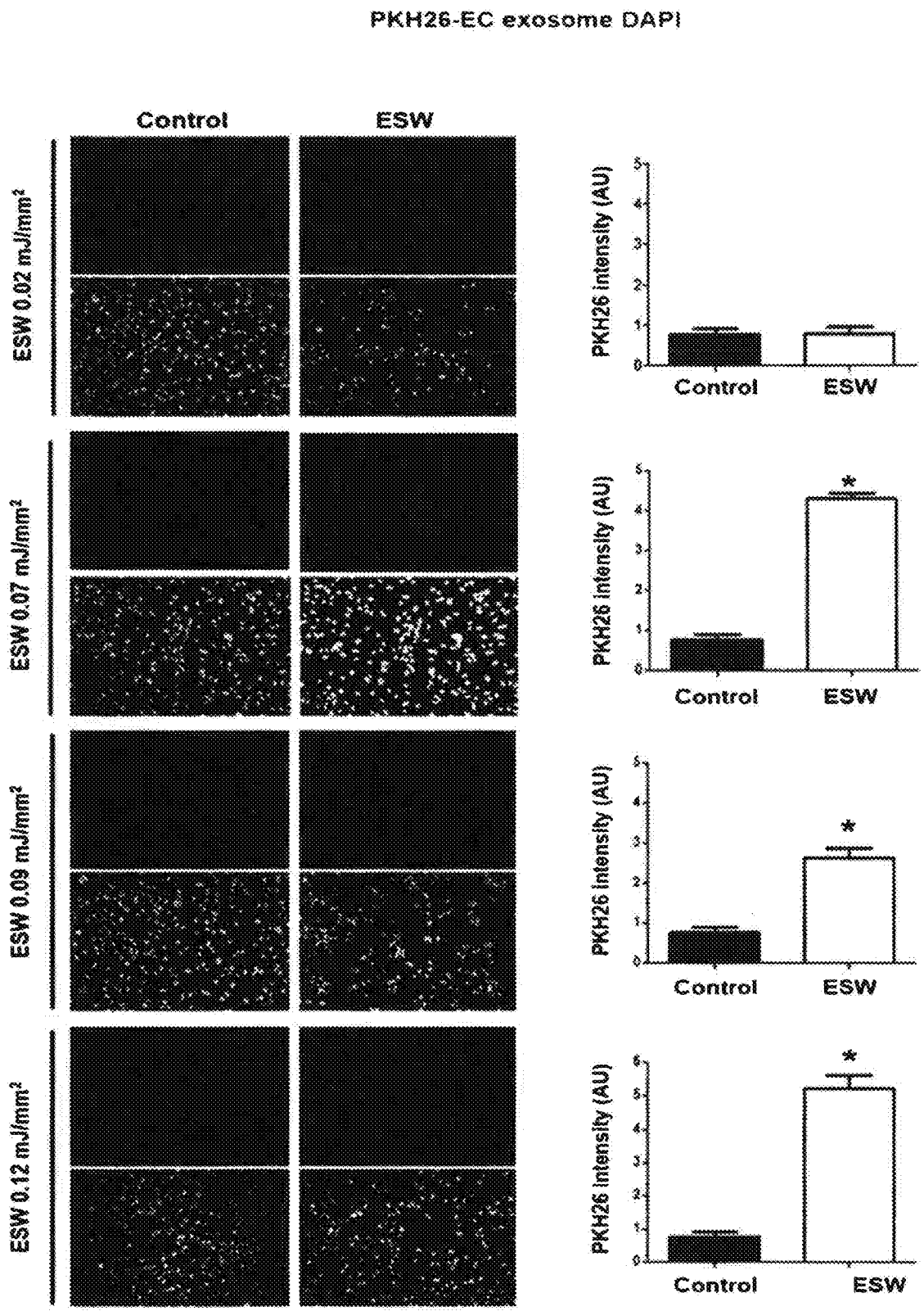
FIG. 3 is a view illustrating the results of a comparative analysis, according to energy levels, of the degree of incorporation of exosomes into cells by extracorporeal shockwaves after HUVECs, human vascular endothelial cells, are treated with exosomes which are derived from HUVECs treated with extracorporeal shockwaves.

As illustrated in FIG. 3, when the extracorporeal shockwave energy level was 0.02 $mJ/mm^2$, no change of the exosome's incorporation into cells by extracorporeal shockwave treatment was observed. On the other hand, in the exosome experimental groups treated with extracorporeal shockwave at an energy level of 0.07 $mJ/mm^2$ to 0.12 $mJ/mm^2$, the exosome's incorporation into the HUVEC cells was significantly prominent compared with the control groups. Therefore, the results demonstrated the quantitative increase of incorporation ability of human cell-derived exosomes into the desired cells when the exosome was treated with the extracorporeal shockwave. Thus, changes in physical properties of exosomes due to extracorporeal shockwave treatment were confirmed.

Example 3. Introduction of Various Target Materials into Exosome by Extracorporeal Shockwave and Confirmation of Transformation Thereby 3.1 Introduction of siRNA (siGlo) into Exosome by Extracorporeal Shockwave and Confirmation of Transformation Thereby The extracorporeal shockwave can be used to introduce various target materials into exosomes with excellent efficiency. The exosomes into which the various target materials were introduced were treated with the extracorporeal shockwave to confirm whether incorporation into other cells also increases, thereby delivering the target materials into the desired cells. An experiment was conducted in which the target material was siGlo, one of the siRNAs. 50 nM siGlo labeled with the red color and exosomes derived from HUVEC, vascular endothelial cell, isolated in Example 1 were mixed. In control groups, there were no extracorporeal shockwave treatments. In addition, extracorporeal shockwave treatments were performed with various energy levels at 0.02 $mJ/mm^2$, 0.07 $mJ/mm^2$, 0.09 $mJ/mm^2$ and 0.12 $mJ/mm^2$, respectively in experimental groups. Then, HUVECs, human vascular endothelial cells, were treated with the extracorporeal shockwave-treated exosome. After one hour, the exosome's incorporation into the desired cells according to the extracorporeal shockwave energy level was compared and analyzed. The results of the experiment are illustrated in FIG. 4.

Figure 4:
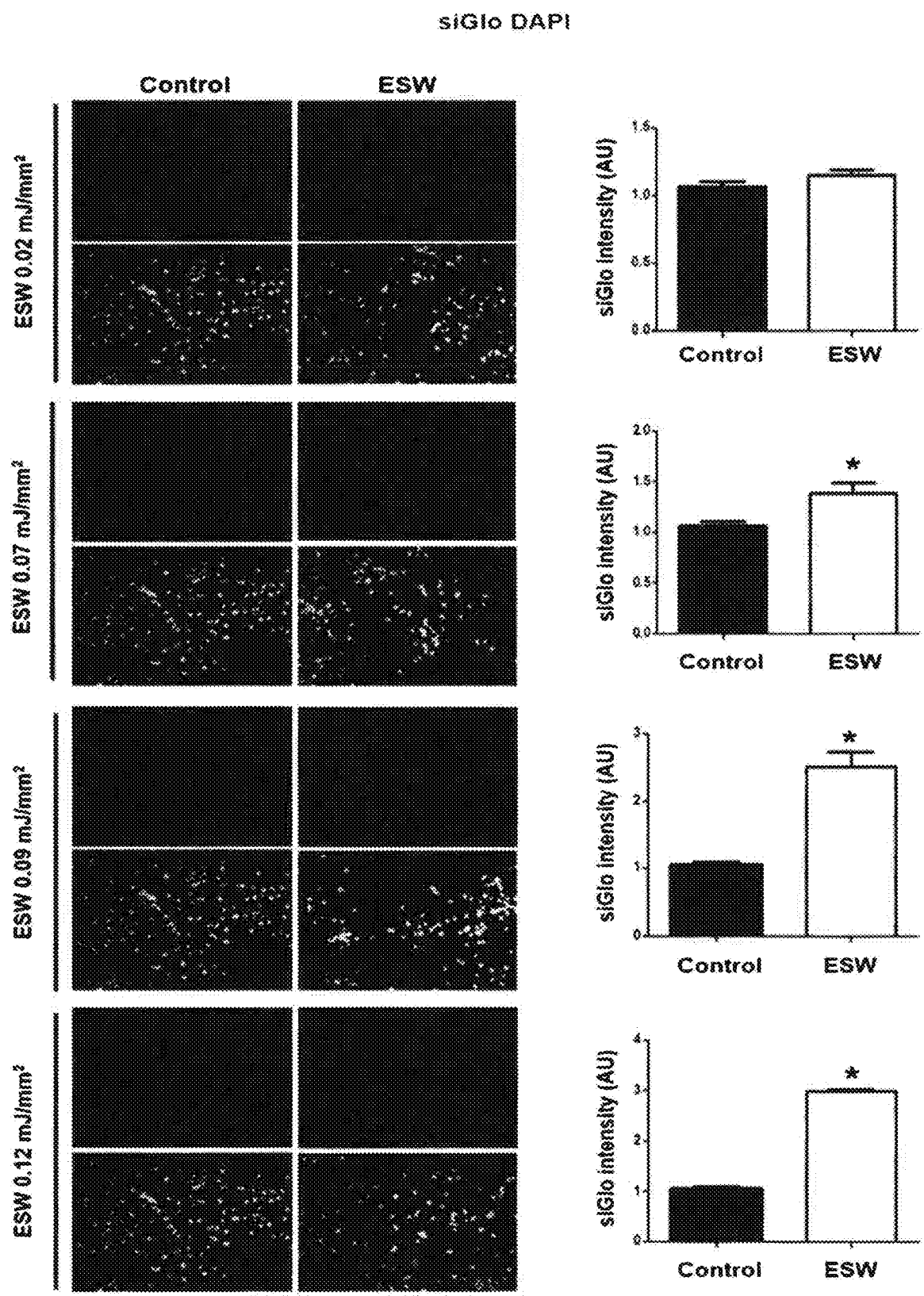
FIG. 4 is a view illustrating the results of comparative analysis of the introduction of siRNA (siGlo) into exosomes by extracorporeal shockwaves having various levels and incorporation ability of the siRNA-introduced exosomes.

As illustrated in FIG. 4, when the extracorporeal shockwave energy level was 0.02 $mJ/mm^2$, there was no change of exosome's incorporation into the cells with or without extracorporeal shockwave treatment. On the other hand, in the exosome experimental groups treated with an extracorporeal shockwave of 0.07 $mJ/mm^2$ or more as other energy levels, exosome's incorporation into the cells was significantly increased compared with the control groups. Thus, when the extracorporeal shockwave treatment of 0.07 $mJ/mm^2$ or more was applied, it was confirmed that the introduction of siGlo, a target material, into exosomes was increased, and the incorporation of the exosomes themselves into the cells was able to be quantitatively increased at the same time. Therefore, it was confirmed that the extracorporeal shockwave was used to deliver the target material introduced into the exosome into the desired cell.

3.2 Introduction of RFP Protein into Exosome by Extracorporeal Shockwave and Confirmation of Transformation Thereby The extracorporeal shockwave can be used to introduce various target materials into exosomes with excellent efficiency. The exosomes into which the various target materials were introduced were treated with the extracorporeal shockwave to confirm whether incorporation into other cells also increases, thereby delivering the target materials into the desired cells. An experiment was conducted in which the target material was RFP, a protein. 2 µg RFP having red color and exosomes derived from HUVEC, vascular endothelial cell, isolated in Example 1 were mixed. In control groups, there were no extracorporeal shockwave treatments. In addition, extracorporeal shockwave treatments were performed with various energy levels at 0.02 $mJ/mm^2$, 0.07 $mJ/mm^2$, 0.09 $mJ/mm^2$ and 0.12 $mJ/mm^2$, respectively in experimental groups. Then, HUVECs, human vascular endothelial cells, were treated with the extracorporeal shockwave-treated exosome. After one hour, the exosome's incorporation into the desired cells according to the extracorporeal shockwave energy level was compared and analyzed. The results of the experiment are illustrated in FIG. 5.

Figure 5:
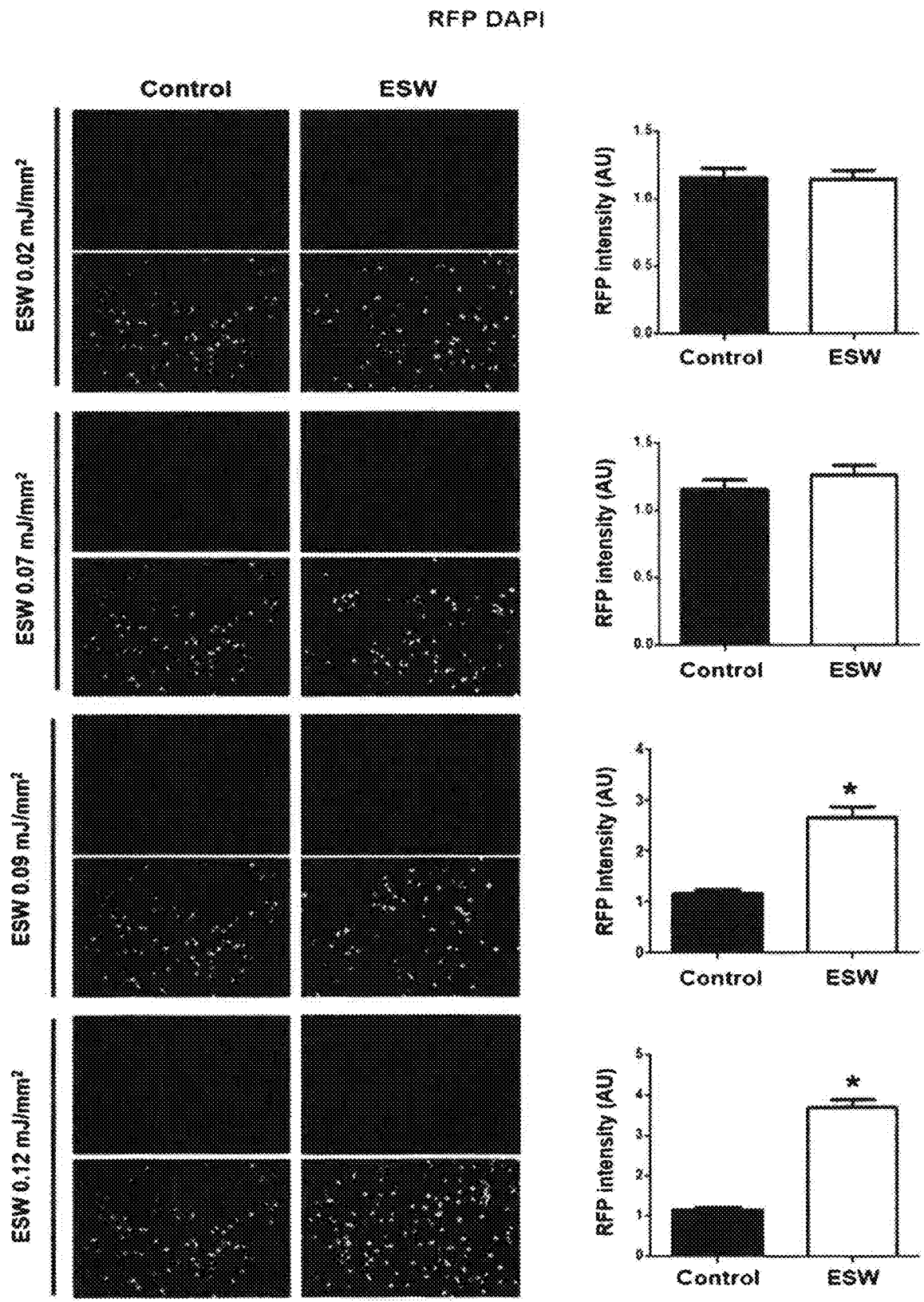
FIG. 5 is a view illustrating the results of comparative analysis of the introduction of RFP proteins into exosomes by extracorporeal shockwaves having various levels and incorporation ability of the protein-introduced exosomes.

As illustrated in FIG. 5, when the extracorporeal shockwave energy level was 0.02 $mJ/mm^2$, there was no change of exosome's incorporation into the cells with or without extracorporeal shockwave treatment. On the other hand, in the exosome experimental groups treated with an extracorporeal shockwave of 0.09 $mJ/mm^2$ or more as other energy levels, exosome's incorporation into the cells was significantly increased compared with the control groups. Thus, when the extracorporeal shockwave treatment of 0.09 $mJ/mm^2$ or more was applied, it was confirmed that the introduction of RFP protein, a target material, into exosomes was increased, and the incorporation of the exosomes themselves into the cells was able to be quantitatively increased at the same time. Therefore, it was confirmed that the extracorporeal shockwave was used to efficiently deliver the target material introduced into the exosome into the desired cell.

3.3 Introduction of microRNA into Exosome by Extracorporeal Shockwave and Confirmation of Transformation Thereby The extracorporeal shockwave can be used to introduce various target materials into exosomes with excellent efficiency. The exosomes into which the various target materials were introduced were treated with the extracorporeal shockwave to confirm whether incorporation into other cells also increases, thereby delivering the target materials into the desired cells. An experiment was conducted in which the target material was microRNA. 50 nM microRNA mimic labeled with green color and exosomes derived from HUVEC, vascular endothelial cell, isolated in Example 1 were mixed. In control groups, there were no extracorporeal shockwave treatments. In addition, extracorporeal shockwave treatments were performed with various energy levels at 0.02 mJ/mm$^2$, 0.07 mJ/mm$^2$, 0.09 mJ/mm$^2$ and 0.12 mJ/mm$^2$, respectively in experimental groups. Then, HUVECs, human vascular endothelial cells, were treated with the extracorporeal shockwave-treated exosome. After one hour, the exosome's incorporation into the desired cells according to the extracorporeal shockwave energy level was compared and analyzed. The results of the experiment are illustrated in FIG. 6.

Figure 6:
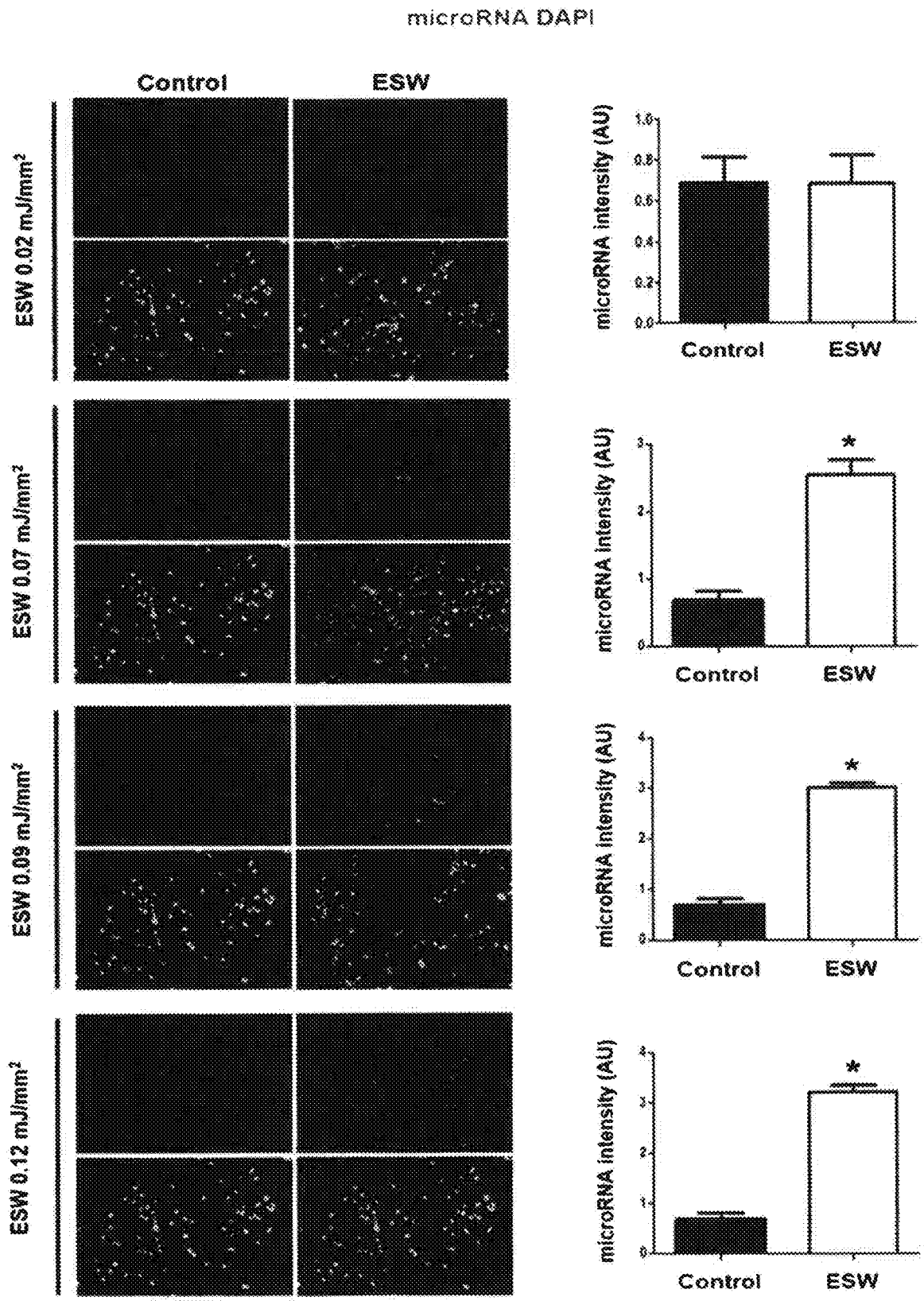
FIG. 6 is a view illustrating the results of comparative analysis of the introduction of microRNA into exosomes by extracorporeal shockwaves having various levels and incorporation ability of the microRNA-introduced exosomes.

As illustrated in FIG. 6, when the extracorporeal shockwave energy level was 0.02 mJ/mm$^2$, there was no change of exosome's incorporation into the cells with or without extracorporeal shockwave treatment. On the other hand, in the exosome experimental groups treated with an extracorporeal shockwave of 0.07 mJ/mm$^2$ or more as other energy levels, exosome's incorporation into the cells was significantly increased compared with the control groups. Further, it was confirmed that the incorporation of the exosomes themselves into the cells was increased at least twice quantitatively. Thus, when the extracorporeal shockwave treatment of 0.07 mJ/mm$^2$ or more was applied, it was confirmed that the introduction of microRNA, a target material, into exosomes was increased, and the incorporation of the exosomes themselves into the cells was quantitatively increased at the same time. Therefore, it was confirmed that the extracorporeal shockwave was used to efficiently deliver the target material introduced into the exosome into the desired cell.

Example 4. Confirmation of Introduction of Nucleic Acid into Various Cells-Derived Exosome by Extracorporeal Shockwave and Efficiency of Cell Transformation by Nucleic Acid-Introduced Exosome 4.1 Introduction of Nucleic Acid into Various Cells-Derived Exosome by Extracorporeal Shockwave Exosomes isolated from human umbilical vein endothelial cells, mesenchymal stem cells, and vascular smooth muscle cells (VSMC) were centrifuged at 3,000 g for 30 minutes to be concentrated. Then, the resultants were used after a nanoparticle tracing analysis (NTA) was performed to identify the same. 2 ml of medium composition, 2 μM *Caenorhabditis elegans* miR-39 (Cel-miR-39) and 1×10$^{-8}$ cells/ml of exosomes derived from HUVEC, MSC or VSMC were mixed in a conical tube. The mixture was treated with an extracorporeal shockwave of 1,000 shots at an intensity of 0.07 mJ/mm$^2$ for 4 minutes, thereby obtaining nucleic acid-introduced exosomes. The exosome obtained without the extracorporeal shockwave was used as a control group. FBS, which was centrifuged at 32,000 rpm for 1 hour and 30 minutes, was used in the exosome isolation experiments. Thus, the experiment was performed without exosomes already present since the exosomes were removed in the cell culture.

Figure 7:
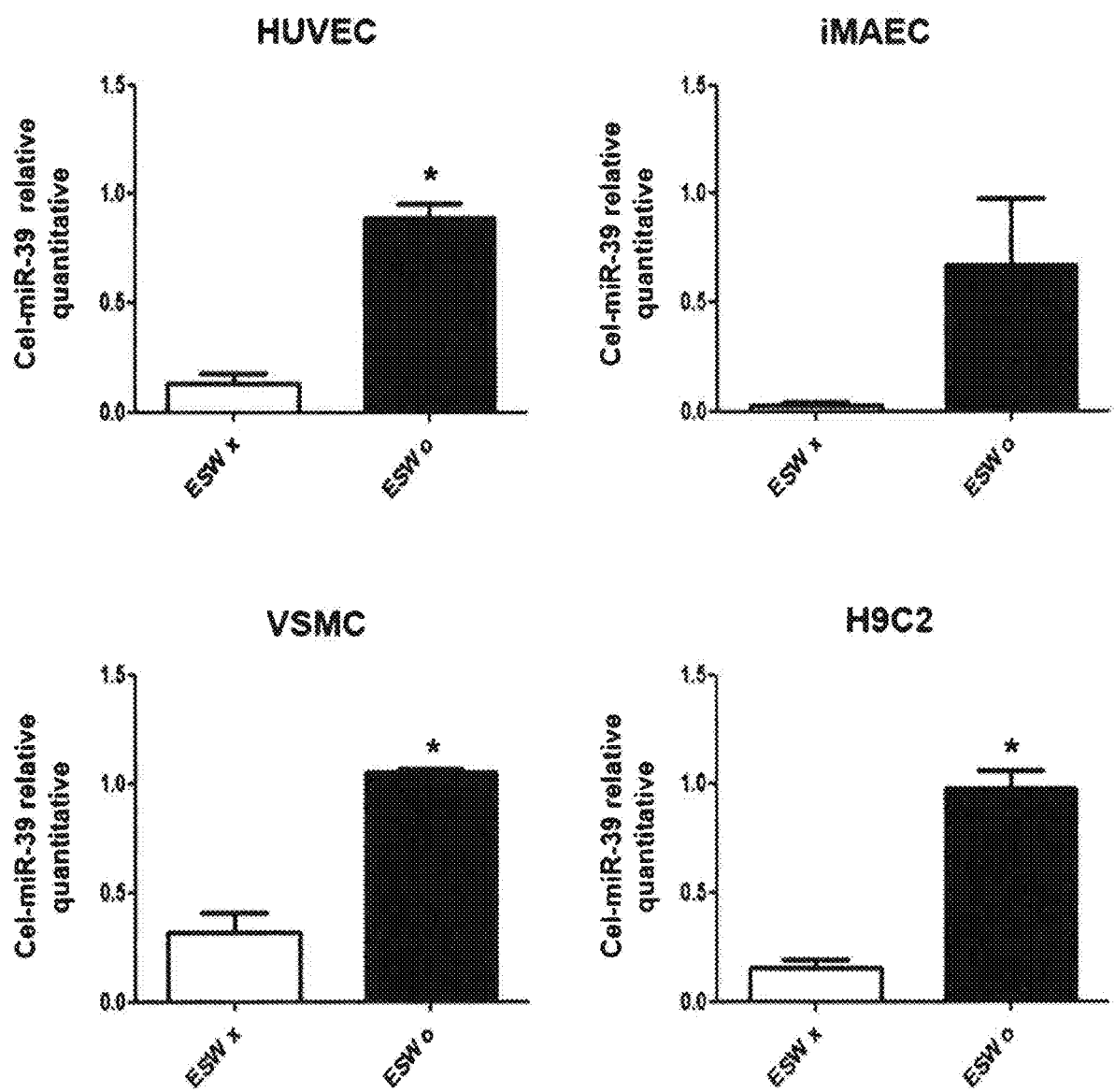
FIG. 7 is a view illustrating the results of comparing the transformation rate of microRNA (Cel-miR-39) using HUVEC-derived extracellular vesicles into which nucleic acids are introduced by extracorporeal shockwaves (ESW O) with control groups (ESW X) for various cells.

4.2. Confirmation of Efficiency of Transformation by Nucleic Acid-Introduced Exosome by Extracorporeal Shockwave 4.2.1. Confirmation of Delivery of Nucleic Acid into Various Cells by HUVEC-Derived Exosome and Efficiency of Transformation First, HUVECs, immortalized mouse aortic endothelial cells (iMAECs) and VSMCs or H9C2 cells which are cardiomyocyte cell lines were seeded in a 6-well plate at a concentration of 4×10$^5$ cells/well, respectively. The cells were incubated for 24 hours. Then, the HUVEC-derived exosome prepared in Example 4.1 was added at 1×10$^{-8}$ cells/ml per well. The cells including exosomes were incubated at 37° C. for 1 hour, washed with PBS, added with 2 ml of medium per well, and further incubated for 24 hours, thereby obtaining incubated cells. According to a conventional method, a QIAzol (QIAzen) was used to extract RNA from the cells. The extracted RNA was quantitated using a nanodrop (NanoDrop Technologies Inc., USA) by an ultraviolet absorption wavelength of 260 nm. Diethyl pyrocarbonic acid (DEPC)-added distilled water was added to the quantified RNA, resulting in RNA concentration of 1 μg/μl. 10 μl of RNA and DEPC distilled water were mixed. 4 μl of 5× miScript HiFlex buffer (QIAGEN, Germany), 2 μl of 10× miScript Nucleics Mix (QIAGEN, Germany), and 2 μl of 10× miScript Reverse Transcriptase Mix (QIAGEN, Germany) were added to the mixture. Then, the reverse transcription reaction thereof was performed at 37° C. for 1 hour. 2 μl of the primer shown in the following Table 1, 2 μl of 10× miScript Universal primer (QIAGEN, Germany), 10 μl of 2× SYBRGreen I mixture (Applied Biosystems), and 5 μl of distilled water were added to 1 μl of the synthesized cDNA. Real-time PCR on the mixture was performed using ABI 7900HT (Applied Biosystems) in a conventional method. Then, the expression level of Cel-miR-39 was measured in which Cel-miR-39 can confirm the delivery by exosomes when it is detected in the target cell because it is not present in human cells. The results of measuring expression levels are illustrated in FIG. 7. In this Example, the microRNA expression level was quantitated based on RNU-6 which is the internal control group. All experiments were performed three times. The results were shown as average values obtained by Mann-Whitney U test.

TABLE 1

Primers used in real-time PCR

| Primers | Primer secquennes (5'→3') |
|---|---|
| U6-Fw (SEQ ID NO: 1) | TCGCTTCGGCAGCACA |
| Mature Cel-miR-39 (SEQ ID NO: 2) | AGCTGATTTCGTCTTGGTAATA |

As illustrated in FIG. 7, HUVECs, iMAECs, VSMCs and H9C2 cells treated with exosomes derived from HUVECs into which microRNAs were introduced due to extracorporeal shockwave exhibited a significant increase in the expression level of Cel-miR-39 compared with the control group. In other words, the extracorporeal shockwave of 0.07 mJ/mm$^2$ or more was applied to introduce the nucleic acid into exosomes which are extracellular vesicles, resulting in excellent efficiency and introduction into various cells compared with groups without the extracorporeal shockwave treatment.

4.2.2. Confirmation of Delivery of Nucleic Acid into Various Cells by MSC-Derived Exosome and Efficiency of Transformation The conditions and methods described in Example 4.2.1 were used to perform this experiment except for the addition of the MSC-derived exosome prepared in Example 4.1 to HUVECs, MSCs or VSMCs. The results of carrying out the experiment are illustrated in FIG. 8.

Figure 8:
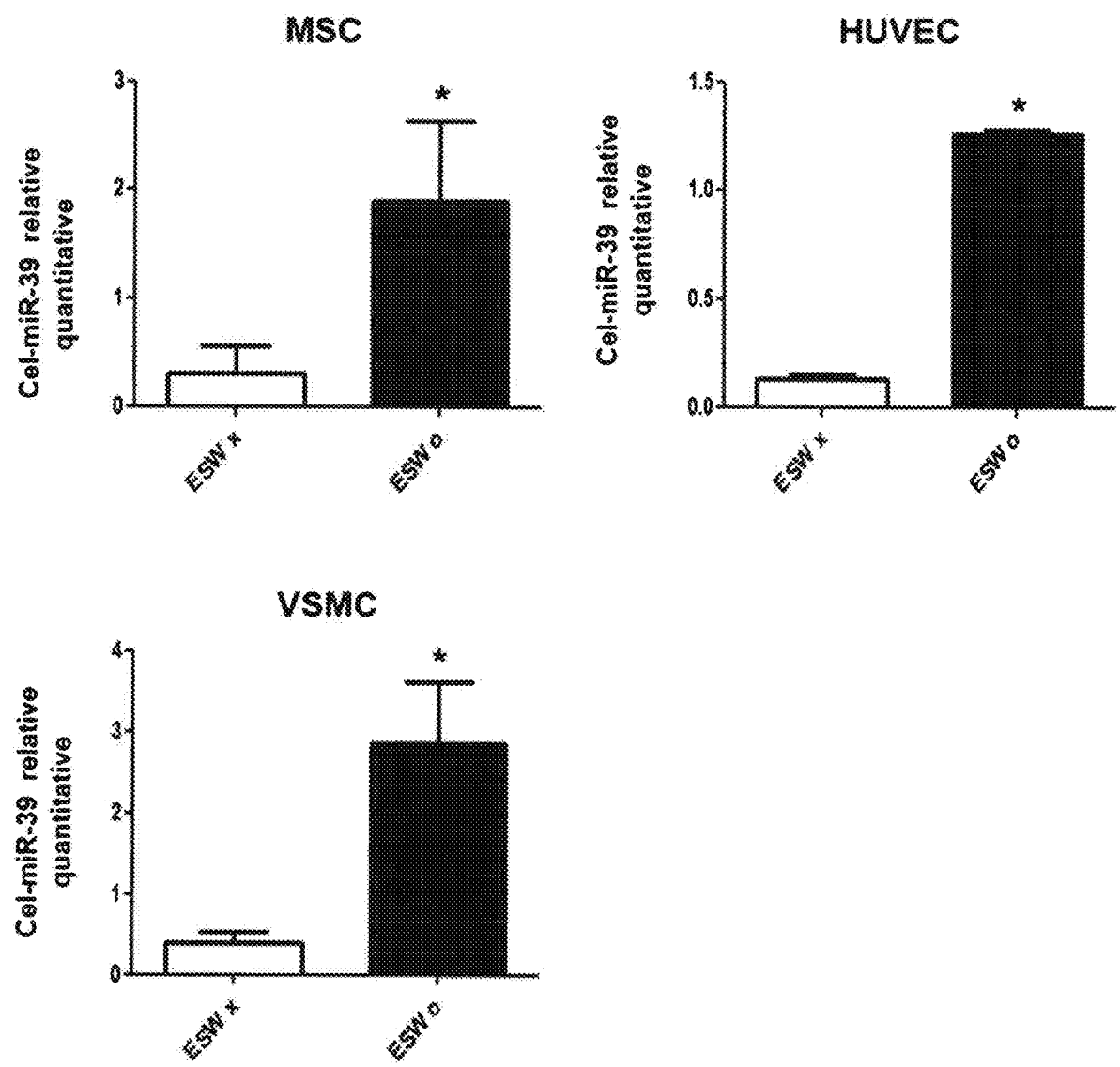
FIG. 8 is a view illustrating the results of comparing the transformation rate of microRNA (Cel-miR-39) using MSC-derived extracellular vesicles into which nucleic acids are introduced by extracorporeal shockwaves (ESW O) with control groups (ESW X) for various cells.

As illustrated in FIG. 8, HUVECs, MSCs and VSMCs treated with exosomes derived from MSCs into which microRNAs were introduced due to extracorporeal shockwave showed a significant increase three times, in the expression level of Cel-miR-39 compared with the control group. In other words, the extracorporeal shockwave of 0.07 mJ/mm$^2$ or more was applied to the HUVEC-derived exosome as well as the MSC-derived exosome so as to introduce the nucleic acid into the MSC-derived exosome, resulting in excellent efficiency and transformation into various cells compared with groups without the extracorporeal shockwave treatment.

4.2.3. Confirmation of Delivery of Nucleic Acid into Various Cells by VSMC-Derived Exosome and Efficiency of Transformation The conditions and methods described in Example 4.2.1 were used to perform this experiment except for the addition of the VSMC-derived exosome prepared in Example 4.1 to HUVECs, iMAECs or VSMCs. The results of carrying out the experiment are illustrated in FIG. 9.

Figure 9:
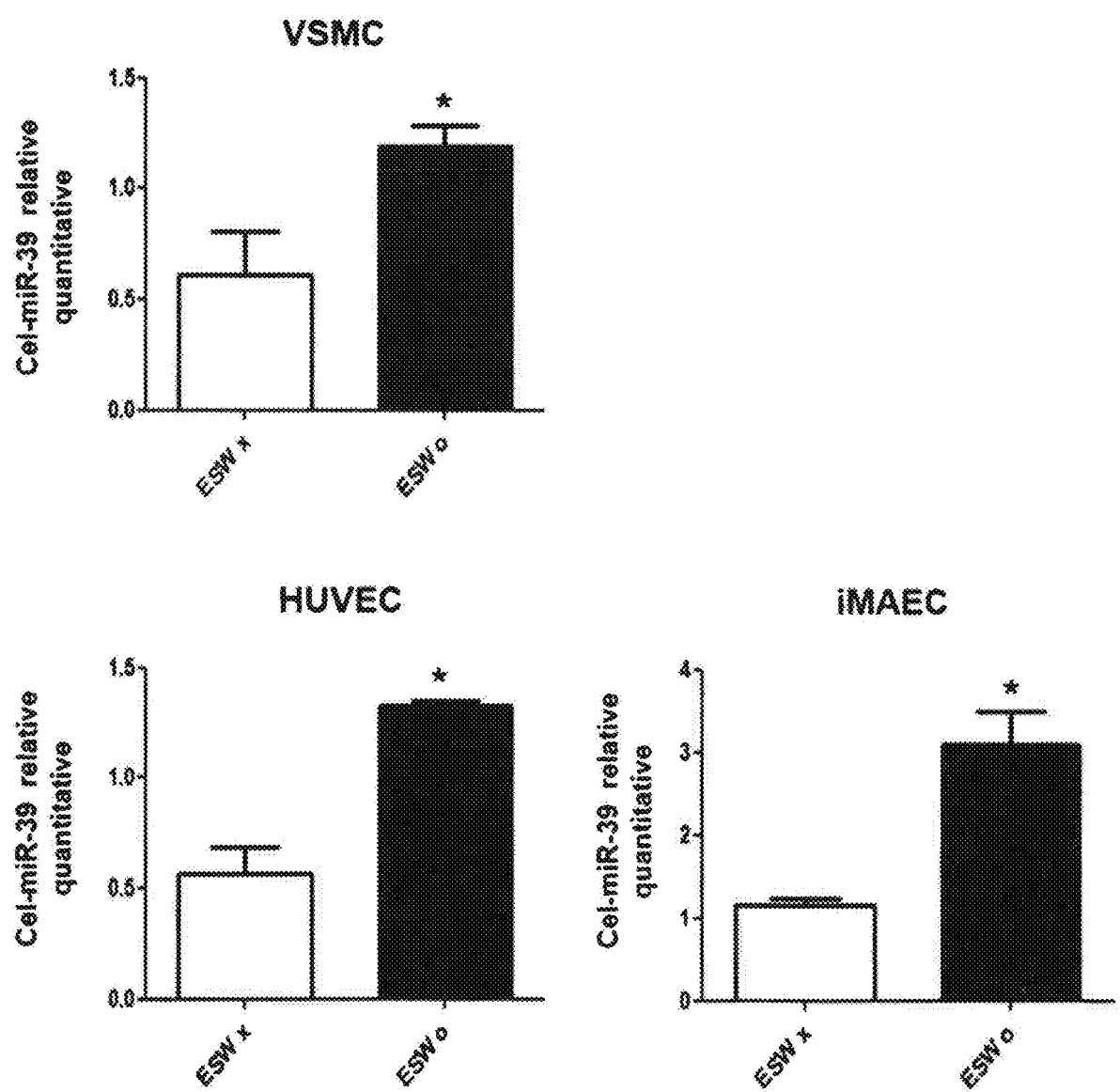
FIG. 9 is a view illustrating the results of comparing the transformation rate of microRNA (Cel-miR-39) using VSMC-derived extracellular vesicles into which nucleic acids are introduced by extracorporeal shockwaves (ESW O) with control groups (ESW X) for various cells.

As illustrated in FIG. 9, HUVECs, iMAECs and VSMCs treated with exosomes derived from VSMCs into which microRNAs were introduced due to extracorporeal shockwave showed a significant increase in the expression level of Cel-miR-39 compared with the control group. Therefore, the extracorporeal shockwave of 0.07 mJ/mm$^2$ or more was applied so as to introduce the nucleic acid into the VSMC-derived exosome, resulting in excellent efficiency and transformation into various cells compared with groups without the extracorporeal shockwave treatment.

Example 5. Confirmation of Transformation Efficiency of Exosome Derived from Various Sources by Extracorporeal Shockwave Treatment 5.1 Confirmation of Transformation Efficiency of Animal-Derived Exosome by Extracorporeal Shockwave In order to confirm whether the incorporation of exosomes into cells is increased when exosomes obtained from other sources than human cells are treated with extracorporeal shockwave, an experiment was carried out in which exosomes were isolated from milk which is one of the animal-derived materials obtaining many exosomes. The milk-derived exosomes isolated in Example 1 were put into wells to be 3×10$^9$ cells per well. The exosomes were stained with PKH26. The control group was a group without extracorporeal shockwave treatment. The experimental group was a group which was treated with the extracorporeal shockwave having an energy level of 0.07 mJ/mm$^2$. Then, HUVECs, human vascular endothelial cells, were treated with the extracorporeal shockwave-treated exosome. After one hour, the incorporation of exosomes into desired cells depending on the extracorporeal shockwave energy level was compared and analyzed. The results of the experiment are illustrated in FIG. 10.

Figure 10:
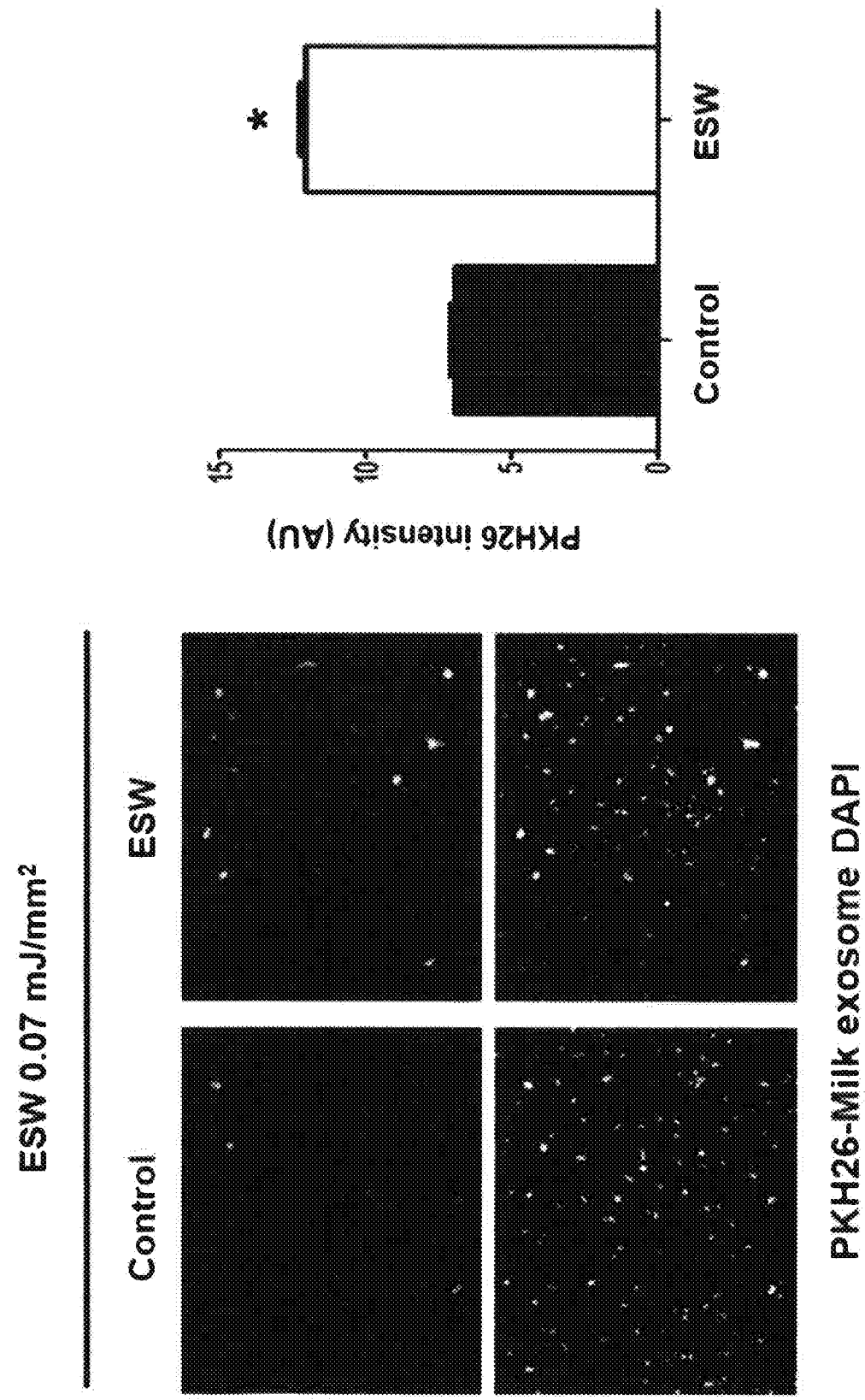
FIG. 10 is a view illustrating the results of comparing, with control groups, the degree of incorporation of exosomes into cells by extracorporeal shockwaves after HUVECs, human vascular endothelial cells, are treated with exosomes which are derived from milk treated with extracorporeal shockwaves.

As illustrated in FIG. 10, exosomes treated with extracorporeal shockwave having an energy level of 0.07 mJ/mm$^2$ showed an increase twice in incorporation into vascular endothelial cells compared with the control group without extracorporeal shockwave treatment. Therefore, incorporation of exosomes into cells was quantitatively increased even when the animal-derived exosome was treated with extracorporeal shockwave.

5.2 Confirmation of Transformation Efficiency of Plant-Derived Exosome by Extracorporeal Shockwave In order to confirm whether the incorporation of exosomes into cells is increased when exosomes obtained from other sources than human cells are treated with extracorporeal shockwave, an experiment was carried out in which exosomes were isolated from grapefruit which is one of the plant-derived materials obtaining many exosomes. The grapefruit-derived exosomes isolated in Example 1 were put into wells to be 3×10$^9$ cells per well. The exosomes were stained with PKH26. The control group was a group without extracorporeal shockwave treatment. The experimental group was a group which was treated with the extracorporeal shockwave having an energy level of 0.07 mJ/mm$^2$. Then, HUVECs, human vascular endothelial cells, were treated with the extracorporeal shockwave-treated exosome. After one hour, the incorporation of exosomes into desired cells depending to the extracorporeal shockwave energy level was compared and analyzed. The results of the experiment are illustrated in FIG. 11.

Figure 11:
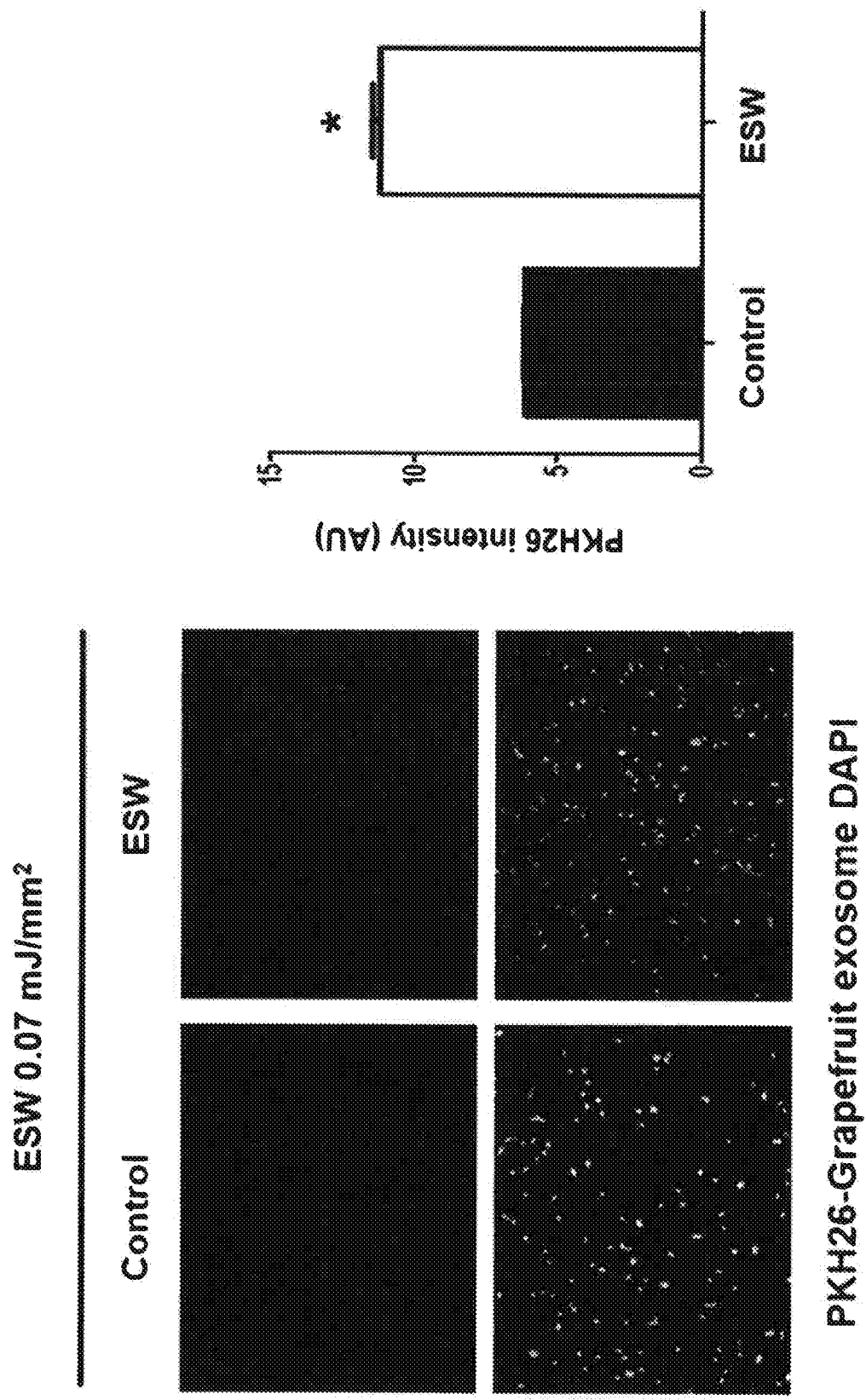
FIG. 11 is a view illustrating the results of comparing, with control groups, the degree of incorporation of exosomes into cells by extracorporeal shockwaves after HUVECs, human vascular endothelial cells, are treated with exosomes which are derived from grapefruit treated with extracorporeal shockwaves.

As illustrated in FIG. 11, exosomes treated with extracorporeal shockwave having an energy level of 0.07 mJ/mm$^2$ showed an increase twice in incorporation into vascular endothelial cells compared with the control group without extracorporeal shockwave treatment. Therefore, incorporation of exosomes into cells was quantitatively increased even when the plant-derived exosome represented by grapefruit was treated with extracorporeal shockwave.

In conclusion, treating with the extracorporeal shockwave having an energy level of 0.07 mJ/mm$^2$ or more results in an increase in the delivery rate of target materials into desired cells for exosomes of different origins. Thus, it is confirmed that the method of the present disclosure is a universally usable technology regardless of exosome origins.

From the foregoing, it will be appreciated that various embodiments of the present disclosure have been described herein for purposes of illustration and that various modifications may be made without departing from the scope and spirit of the present disclosure. Accordingly, the various embodiments disclosed herein are not intended to be limiting, with the true scope and spirit being indicated by the following claims.

What is claimed is:

1. A method of delivering a target material into an isolated extracellular vesicle, the method comprising:

exposing the target material and the isolated extracellular vesicle to an extracorporeal shockwave for i) increasing a number of the isolated extracellular vesicle, ii) increasing properties of at least one selected from the group consisting of zeta potential of the isolated extracellular vesicle and an ability of incorporation of the isolated extracellular vesicle into cells, and iii) delivering the target material into the isolated extracellular vesicle.

2. The method of claim 1, wherein the target material includes at least one selected from the group consisting of a nucleic acid, a protein, and a compound.

3. The method of claim 1, wherein the extracorporeal shockwave has an energy range from 0.05 mJ/mm$^2$ to 0.9 mJ/mm$^2$.

4. The method of claim 1, wherein the extracellular vesicle includes at least one selected from the group consisting of an exosome, an ectosome, a microvesicle, and an apoptotic body.

5. A method of preparing a target material-introduced extracellular vesicle, the method comprising:

exposing an target material and an isolated extracellular vesicle to an extracorporeal shockwave for i) increasing a number of the isolated extracellular vesicle, ii) increasing properties of at least one selected from the group consisting of zeta potential of the isolated extracellular vesicle and an ability of incorporation of the isolated extracellular vesicle into cells, and iii) delivering the target material into the isolated extracellular vesicle.

* * * * *